(12) United States Patent
Lieberman et al.

(10) Patent No.: US 9,776,731 B1
(45) Date of Patent: Oct. 3, 2017

(54) METHODS AND APPARATUS FOR DETECTING AIRCRAFT SURFACE DEFORMATIONS

(71) Applicant: The Boeing Company, Chicago, IL (US)

(72) Inventors: Eric Howard Lieberman, Broomall, PA (US); William Brendan Blanton, Wilmington, DE (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 15/280,274

(22) Filed: Sep. 29, 2016

(51) Int. Cl.
*B64C 3/52* (2006.01)
*B64D 45/00* (2006.01)
*G08B 21/18* (2006.01)

(52) U.S. Cl.
CPC ............. *B64D 45/00* (2013.01); *G08B 21/18* (2013.01)

(58) Field of Classification Search
CPC .............................. Y02T 50/12; Y02T 50/145
USPC ................................. 340/963, 968, 969, 970
See application file for complete search history.

(56) References Cited

U.S. PATENT DOCUMENTS

2015/0329216 A1* 11/2015 Laurens ................. B64D 43/02
  701/6
2016/0059968 A1*  3/2016 Bredemeier .......... B64C 1/1407
  701/34.4

OTHER PUBLICATIONS

Aerospace Daily & Defense Report, "Osprey Mission Set Grows As Safety Concerns Linger," Sep. 1, 2016, last accessed on Apr. 12, 2017, [http://www.aviationweek.com/awindefense/osprey-mission-set-grows-safety-concerns-linger], 6 pages.

* cited by examiner

*Primary Examiner* — Kevin Kim
(74) *Attorney, Agent, or Firm* — Hanley, Flight & Zimmerman, LLC

(57) ABSTRACT

Methods and apparatus for detecting surface deformation of aircraft surfaces are disclosed. An example apparatus includes a sensor system to monitor an aircraft surface, the sensor system including a first sensor and a second sensor. A surface monitoring system receives signals from the first sensor and the second sensor and based on the signals received, the surface monitoring system is to: detect a surface deformation on the aircraft surface; analyze one or more environmental conditions or aircraft parameters; and classify a severity of a detected surface deformation based on the one or more environmental conditions or aircraft parameters to determine if the detected surface deformation impacts aircraft performance or safety.

21 Claims, 9 Drawing Sheets

METHODS AND APPARATUS FOR DETECTING AIRCRAFT SURFACE DEFORMATIONS

FIELD

The present disclosure relates generally to aircraft and, more particularly, to methods and apparatus for detecting aircraft surface deformations.

BACKGROUND

In general, aircraft surfaces may be susceptible to deformation during flight. Surface deformation of an aircraft surface may affect or alter an aerodynamic characteristic(s), which can reduce aircraft performance. For example, deformation of aircraft surfaces may affect (e.g., reduce) lift, engine efficiency, etc., and/or may cause compressor stall or engine flameout. For example, vertical/short take-off and landing (V/STOL) aircraft are fixed-wing aircraft that can lift off, land and/or hover vertically, and can transition from a vertical hover mode to a horizontal flight mode. In some instances, an aerodynamic surface or inlet of such an aircraft, when hovering over certain ground materials and combined with particular atmospheric conditions (e.g., wet sand, moisture content), can be exposed to particulate that cause damage to the aerodynamic surfaces and/or an engine of the aircraft.

SUMMARY

An example apparatus disclosed herein includes a sensor system to monitor an aircraft surface, the sensor system including a first sensor and a second sensor. A surface monitoring system receives signals from the first sensor and the second sensor and, based on the signals received, the surface monitoring system is to: detect a surface deformation on the aircraft surface; analyze one or more environmental conditions or aircraft parameters; and classify a severity of a detected surface deformation based on the one or more environmental conditions or aircraft parameters to determine if the detected surface deformation impacts aircraft performance or safety.

An example method disclosed herein includes monitoring an aircraft surface via a first sensor and a second sensor; receiving signals from the first sensor and the second sensor; detecting a surface deformation on the aircraft surface based on the received signals; analyzing one or more environmental conditions or aircraft parameters; and classifying a severity of a detected surface deformation based on the one or more environmental conditions or aircraft parameters to determine if the detected surface deformation impacts aircraft performance or safety.

An example tangible computer-readable medium disclosed herein includes instructions that, when executed, cause a machine to: monitor an aircraft surface via a first sensor and a second sensor; receive signals from the first sensor and the second sensor; detect a surface deformation on the aircraft surface based on the received signals; analyze one or more environmental conditions or aircraft parameters; and classify a severity of a detected surface deformation based on the one or more environmental conditions or aircraft parameters to determine if the detected surface deformation impacts aircraft performance or safety.

DESCRIPTION

Example methods and apparatus disclosed herein sense or detect aircraft surface deformations. In addition to detecting surface deformation, the example methods and apparatus disclosed herein determine whether aircraft operating condition(s) and/or environmental flight conditions affect aircraft performance based on the detected surface deformation. More specifically, example methods and apparatus disclosed herein analyze information to classify a severity of a detected surface deformation based on one or more parameters (e.g., surface deformation characteristic(s), environmental data, aircraft state or operating parameters, etc.) to determine the likelihood of the detected surface deformation impacting aircraft performance or safety. Thus, the example methods and apparatus disclosed herein significantly increase quality and/or accuracy of detected aerodynamic and/or propulsion system surface conditions based on environmental conditions, thereby enabling a pilot to make a better informed decision as to whether to remain in a detected hazardous condition for a longer or shorter period of time.

Figure 1:
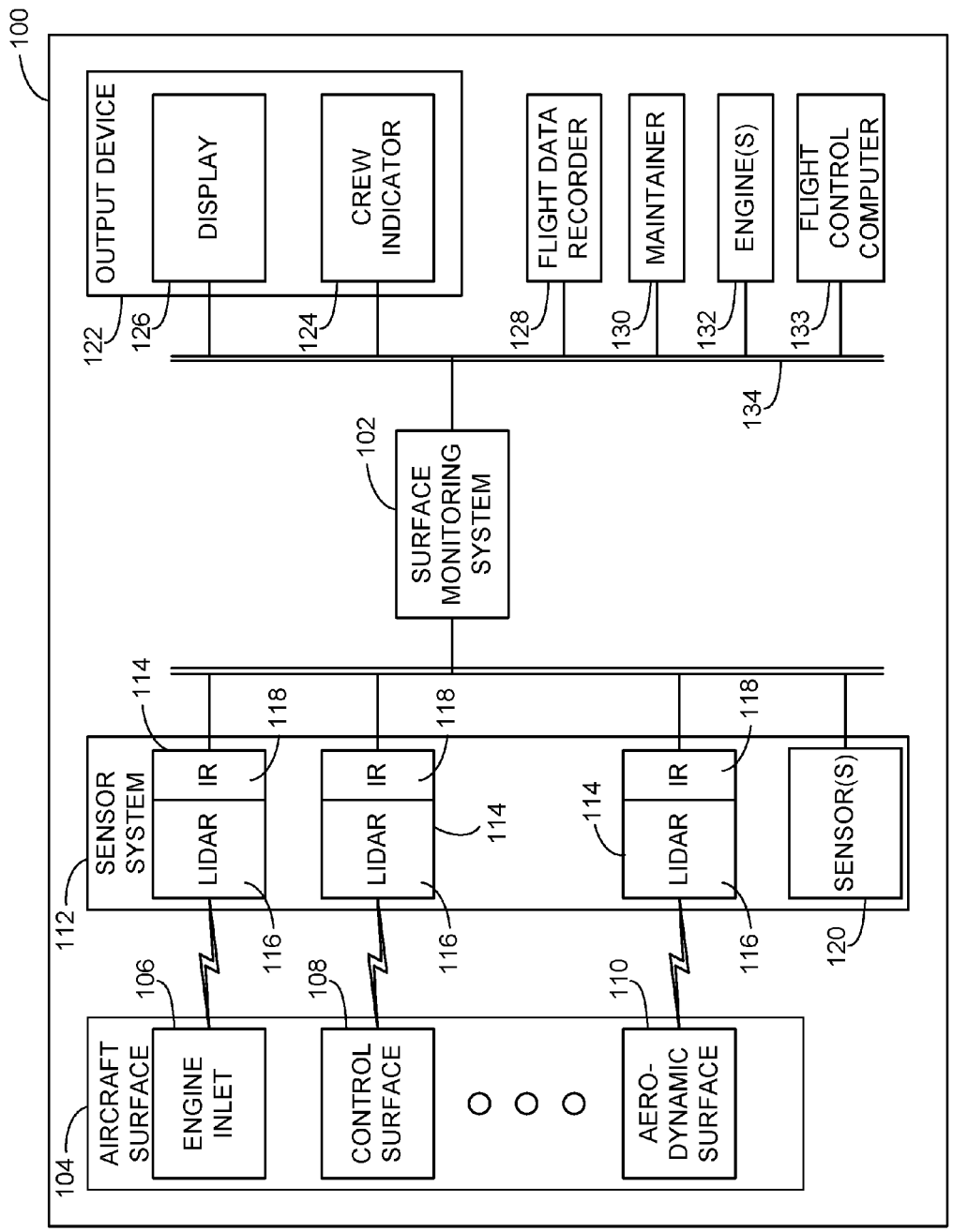
FIG. 1 is a block diagram of an example aircraft implemented with an example surface monitoring system in accordance with the teachings of this disclosure.

FIG. 1 is a block diagram of an example aircraft 100 implemented with an example surface monitoring system 102 constructed in accordance with the teachings of this disclosure. The example surface monitoring system 102 monitors an aircraft surface 104 to detect deformation during flight. For example, the surface monitoring system 102 of the illustrated example detects deformations of the aircraft surface 104 that may affect aircraft performance (e.g., engine efficiency) and/or its effect on aircraft safety.

The aircraft surface 104 of the illustrated example may include, for example, an engine inlet 106, a control surface 108, an aerodynamic surface 110, and/or any other aircraft surface(s) for which surface monitoring is desired. For example, monitoring the engine inlet 106 may include monitoring a surface defining at least a portion of an inlet of an aircraft engine (e.g., a surface upstream or downstream from the inlet). The control surface 108 may include, for example, an aileron, a flap, an elevator, a rudder, a tab, an adjustable surface, a rudder, and/or other flight control mechanism(s). The aerodynamic surface 110 may include, for example, an airfoil of a nacelle, a wing, and/or any other surface such as, for example, a surface of the fuselage, etc. In some examples, the aircraft surface 104 may include, for example, a surface inside an engine (e.g., a surface of a second compressor of an engine), a fan or rotor blade, and/or any other surface of the aircraft 100.

As used herein, the term "surface deformation" includes, but is not limited to, additive deformation of the aircraft surface 104 and/or subtractive deformation of the aircraft surface 104 when compared to an initial or original state of the respective aircraft surface 104 (e.g., an originally manufactured aircraft surface 104). For example, additive deformation may occur due to a buildup or accretion of material(s), particulate(s) of foreign matter(s) on the aircraft surface 104 such that the buildup or accretion of material affects airflow characteristic(s) and/or aircraft performance and/or aircraft safety. For example, accretion of material(s) on the aircraft surface 104 may be caused by dust, particulate, wet sand, dry sand, rotorcraft induced brownout conditions, ice accumulation, fluid accumulation (e.g., hydraulic oil, fuel, transmission fluid, etc.), corrosion, and/or any other material(s). In some examples, subtractive deformation includes, but is not limited to, erosion, cracking, abrasion, removal of material, rotor blade deformation or damage, and/or other damage (e.g., bending or denting) to the aircraft surface 104 that affects an aerodynamic characteristic(s) of the respective aircraft surface 104 that may be caused by, for example, abrasive material(s) (e.g., sand entrained in high velocity airflow), bird strikes, drone strikes, ballistic strikes, thermal deformation, etc. In some examples, surface deformation may include, for example, a volume of material(s), particulate(s) or foreign matter ingested by an engine 132 of the aircraft 100.

To monitor the aircraft surface 104 of the aircraft 100 and/or detect certain environmental or flight conditions, the example surface monitoring system 102 of the illustrated example employs a sensor system 112. In particular, the surface monitoring system 102 of the illustrated example receives and analyzes data from the sensor system 112 to develop current surface data (e.g., point cloud data) corresponding to the monitored aircraft surface 104, determine atmospheric conditions or characteristic(s), determine obscurant conditions, determine aircraft state data and operating parameter(s), etc. The surface monitoring system 102 of the illustrated example compares the current surface data to historical surface data (e.g., initial point cloud data, a plurality of point cloud data gathered during flight, etc.). Based on the comparison of the current surface data and the historical surface data, the surface monitoring system 102 detects the deformation of the aircraft surfaces 104. In some examples, to determine or detect surface deformation, environmental conditions, aircraft operating parameters and/or obscurant conditions, the example surface monitoring system 102 analyzes characteristic(s) of signals from the sensor system 112 including, but not limiting to, intensity, polarization, change in reflectivity of the surface 104, temperature gradient changes of the aircraft surface 104, LIDAR modes (e.g., full wave processing, Raman scattering, etc.) and/or any other characteristic(s).

The sensor system 112 of the illustrated example includes a plurality of sensors 114 to monitor and/or provide data or information regarding a plurality of aircraft surfaces 104 and/or environmental or operating conditions to the surface monitoring system 102. For example, a respective one of the sensors 114 of the illustrated example measures or monitors a point cloud associated with a respective one of the aircraft surfaces 104. For example, the point cloud may be a set of data points defined by x, y, and z coordinates that represent the aircraft surfaces 104 (e.g., may be provided in a tabular format). For example, the point cloud may measure or model contours or shapes of the aircraft surfaces 104 and may be determined by, for example, a 3-D scanner. In turn, the surface monitoring system 102 processes the information from the sensors 114 to determine deformation of the aircraft surfaces 104.

In the illustrated example, a respective one of the sensors 114 monitors a respective one of the aircraft surfaces 104. Thus, each aircraft surface 104 (e.g., the engine inlet 106, the control surface 108, and the aerodynamic surface 110) includes a corresponding dedicated sensor 114. For example, a first one of the sensors 114 monitors (e.g., a point cloud of) the engine inlet 106, a second one of the sensors 114 monitors (e.g., a point cloud of) the control surface 108, and a third one of the sensors 114 monitors (e.g., a point cloud of) the aerodynamic surface 110.

Each sensor 114 of the illustrated example employs a first sensor 116 and a second sensor 118 to detect surface deformation (e.g., accretion of particulate) of the respective one of the monitored aircraft surfaces 104. For example, the first sensor 116 and the second sensor 118 of a first one of the sensors 114 may be configured (e.g., aimed) to monitor the engine inlet 106. In some examples, data from the second sensor 118 may be used to verify or validate data provided by the first sensor 116. In some examples, the surface monitoring system 102 of the illustrated example fuses data from the first sensor 116 and the second sensor 118 to determine, for example, a deformation of the aircraft surface 104 associated with the first sensor 116 and the second sensor 118. For example, the first sensor 116 of the illustrated example includes a laser sensor (e.g., a LIDAR sensor system, a laser 3-D imaging sensor, etc.) and the second sensor 118 of the illustrated example is an infrared sensor. In some examples, the first sensor 116 and/or second sensor 118 may be implemented by other sensors such as, for example, imaging sensors, visual sensors, cameras, terahertz sensors, 3-D scanners, 2-D scanners and/or any other sensor or sensing system(s) to monitor a condition of the aircraft surface 104.

In some examples, the sensors 114 may be used to provide data or information regarding a particulate accreted on the aircraft surface 104. For example, the sensors 114 of the illustrated example may provide density information regarding an accreted material, the type of material(s), a volume of the accreted material, a surface temperature, a surface temperature gradient, and/or any other data or information regarding the accreted material(s).

In some examples, the sensors 114 of the illustrated example may provide air data or flight condition information to the surface monitoring system 102 and/or an engine control system (e.g., a Full Authority Digital Engine Controller (FADEC)) of the aircraft 100. Air data or flight conditions may include information such as airspeed of the aircraft 100, a velocity of air flowing along the aircraft 100 (e.g., an updraft, a downdraft, and/or a sidedraft), a temperature of the air surrounding the aircraft 100, an angle of attack of the aircraft 100, velocities, altitude, barometric data, ram air pressure and static pressure, air density, humidity, attitudes, accelerations, and/or other information associated with the air and/or other environmental or flight conditions. In some examples, the aircraft 100 of the illustrated example may employ other aircraft sensors 120 (e.g., a pressure sensor, a temperature sensor, a pitot-static sensor, an altimeter) to determine air data and/or flight conditions.

In addition to detecting deformation of the aircraft surfaces 104, the example surface monitoring system 102 of the illustrated example determines whether the detected surface deformation affects aircraft performance in view of aircraft operating parameters and/or environmental conditions. For example, if a surface deformation is detected, the example surface monitoring system 102 analyzes a temperature of the aerodynamic surface, detected changes in reflectivity due to particulate matter on the aerodynamic surface, and/or considers obscurant conditions, air temperature, air pressure, altitude, and/or any other parameter(s) to determine if such parameters or conditions affect aircraft performance. For example, the surface monitoring system 102 of the illustrated example may limit a duration for which the aircraft 100 is exposed to certain obscurant conditions. For example, during a detected rotor induced brownout condition, the surface monitoring system 102 may provide information to the crew intended to limit operation of the aircraft 100 in the brownout condition for a specified duration (e.g., 1 minute) if the surface monitoring system 102 detects that the obscurant material(s) is, for example, wet sand of a particular size and density.

In some examples, the surface monitoring system 102 of the illustrated example provides a warning to a pilot or crew based on the detected aircraft surface deformation and/or detected or predicted hazardous environmental flight conditions affect on flight performance. Thus, in some instances, the example surface monitoring system 102 verifies if a detected deformation (e.g., particulate buildup or surface damage) of the aircraft surfaces 104 requires a notification to the pilot based on detected or predicted hazardous environmental flight conditions. Such validation of the aircraft surface condition(s) and/or the environmental conditions reduces false or improper notifications. To this end, the surface monitoring system 102 of the illustrated example significantly increases quality and/or accuracy of detected surface conditions, which enables a pilot to make a better informed decision as to whether to remain in a detected hazardous condition for a longer or shorter period of time and/or abort the flight mission.

Based on the determined surface deformation and/or the environmental conditions, the surface monitoring system 102 of the illustrated example determines the detected surface deformation and/or environmental conditions and classifies a notification corresponding to the determined hazard level. For example, the surface monitoring system 102 may initiate different alerts for different surface deformations and/or environmental condition(s). For example, the surface monitoring system 102 may initiate an advisory alert indicative of surface deformation commencement, a cautionary alert indicative of the surface deformation worsening, or a warning alert indicative of the deformation impacting aircraft performance. For example, the advisory alert may inform a pilot to continue with a flight mission but the conditions exist that may result in a worsening of aircraft performance, the cautionary alert may inform a pilot to proceed with caution and that the pilot may need to move the aircraft away from the area with the hazardous environmental conditions soon (e.g., within 1 minute), and the warning alert may inform the pilot of an imminent dangerous condition and that the pilot may need to move the aircraft away immediately.

The surface monitoring system 102 of the illustrated example may provide a warning to the pilot or crew via a user interface or an output device 122. The output device 122 can be located in a cockpit of the aircraft 100. In some examples, the output device 122 may be implemented, for example, by one or more display devices including a crew indicator 124 (e.g., a light emitting diode (LED)), a display 126 (e.g., a liquid crystal display), a touchscreen, a tactile output device, an audible device (e.g., speaker), a combination thereof, and/or any other output device(s). A warning content provided by the output device 122 can be in the form of colors, audible alerts, tactile alerts (e.g., vibrating a throttle or control stick), etc. For example, the surface monitoring system 102 may cause the crew indicator 124 to illuminate in a green color to represent the advisory alert, a yellow color to represent the cautionary alert, and a red color to represent the warning alert. In some examples, the surface monitoring system 102 may cause an output signal of the output device 122 to vary or change in pattern (e.g., a blinking pattern), intensity, and the like to enhance conspicuity. For example, an output audio signal may be modulated according to at least one or more characteristics including: volume, pitch, periodicity of repetition, or rhythm.

Additionally or alternatively, the surface monitoring system 102 provides surface deformation information to a flight data recorder 128 and/or to a maintainer 130 via a dedicated display, or display page on an MFD, or memory storage device. For example, the system 130 may record data regarding a location of the surface deformation and may cue the maintainer 130 for inspection post-flight. For example, the surface monitoring system 102 of the illustrated example provides fault data to the maintainer 130 to inspect or investigate the aircraft surfaces 104 when a surface deformation that exceeds some threshold is detected by the surface monitoring system 102 during flight. For example, if the surface monitoring system 102 detects an accretion of material (e.g., sand) on the engine inlet 106 or that the engine 132 of the aircraft 100 ingested a certain volume of particulate (e.g., sand) during flight, the surface monitoring system 102 may cause the maintainer 130 to alert maintenance to inspect the engine inlet 106 and/or the engine 132.

Additionally or alternatively, the example surface monitoring system 102 of the illustrated example may provide feedback (e.g., real-time data) to an electronic engine controller of the engine 132 and/or a flight control computer 133 for performance optimization during flight. For example, the surface monitoring system 102 of the illustrated example provides data (e.g., real-time data) regarding surface deformation and monitors the deformation for changes in engine performance and/or control surface characteristic(s). In some examples, an electronic engine controller may adjust another characteristic or a parameter of, for example, the engine 132, and/or any other device in response to the changes in performance characteristic(s) due to the detected aircraft surface deformation. For example, if the surface monitoring system 102 detects surface deformation at the engine inlet 106 of the engine 132, the surface monitoring system 102 may communicate such information to the electronic engine controllers. The electronic engine controllers may alter, for example, a fuel-to-air ratio to enhance or improve engine efficiency or performance on one or more other engines that may otherwise not be affected by the detected surface deformation of the engine inlet 106 on another engine.

In some examples, the surface monitoring system 102 may communicate with, or cause activation of, an anti-icing system of the aircraft 100 (e.g., an environmental control system (ECS)). For example, the surface monitoring system 102 of the illustrated example may cause activation of an anti-icing system when the surface monitoring system 102 of the illustrated example detects surface deformation caused by ice buildup on an airfoil or wing.

The example surface monitoring system 102 may be communicatively coupled to the sensors 114, the output device 122, the flight data recorder 128, the maintainer 130, an electronic engine controller of the engine 132, and/or a flight control computer 133 via a data bus 134. The sensors 114 may be communicatively coupled to the surface monitoring system 102 and/or the surface monitoring system 102 may be communicatively coupled to the electronic engine controller or other aircraft controllers via, for example, a fiber optic cable, a wireless connection, a cellular connection, and/or any other suitable communication system(s). In some examples, the surface monitoring system 102 may be implemented by a full authority digital engine controller (FADEC) and/or the flight control computer 133.

Figure 2:
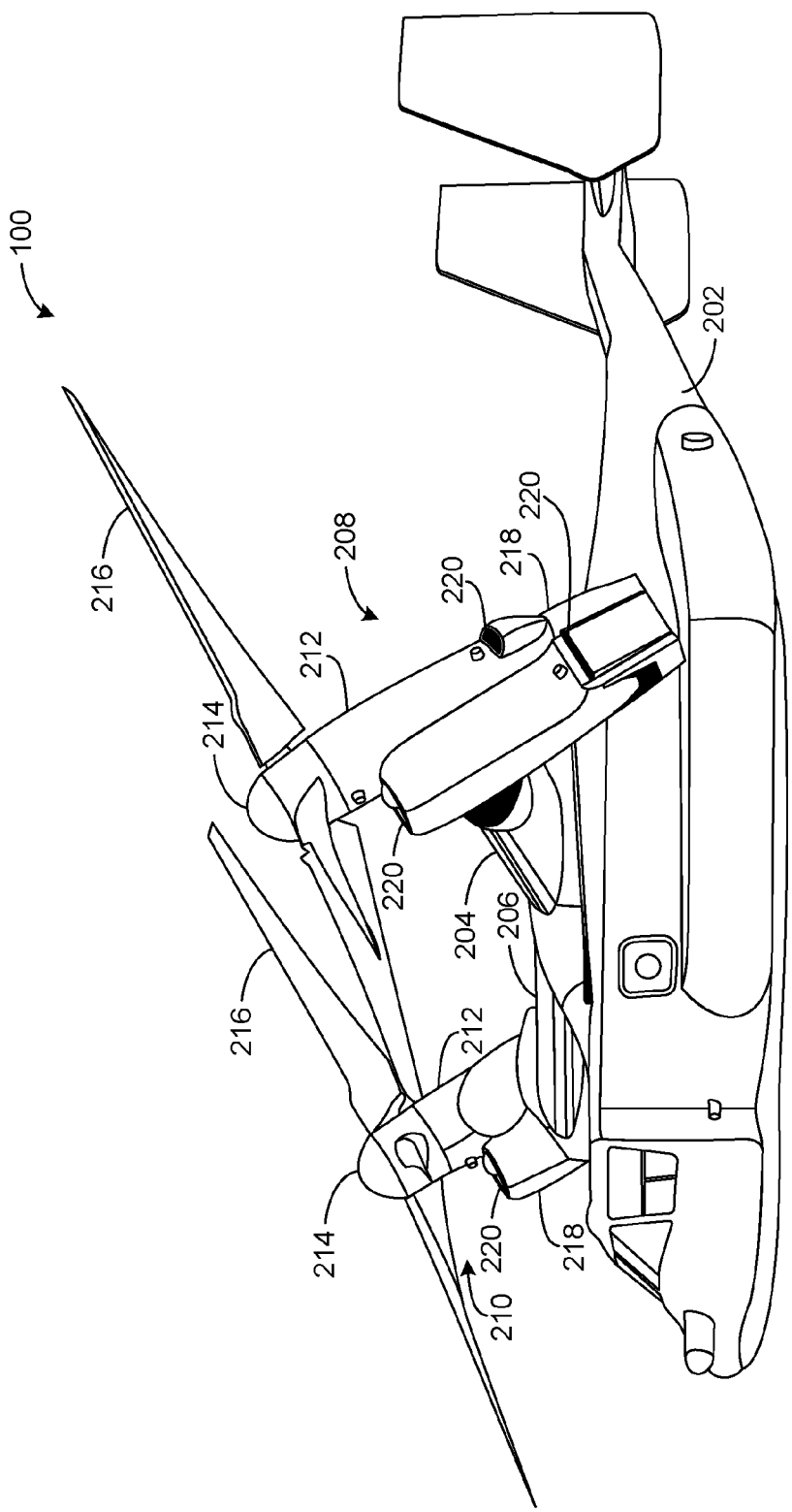
FIG. 2 is a perspective view of the example aircraft of FIG. 1.

FIG. 2 is a perspective view of the example aircraft 100 of FIG. 1. The example aircraft 100 of FIG. 2 is a tilt rotor aircraft (e.g., a V-22 or Osprey aircraft). The aircraft 100 is an example aircraft and, thus, the example methods and apparatus disclosed herein may be implemented with other aircraft (e.g., commercial aircraft, fixed-wing aircraft, rotorcraft, compound aircraft, etc.), spacecraft or vehicles without departing from the scope of this disclosure.

In the illustrated example, the aircraft 100 includes a fuselage 202, a first wing 204 and a second wing 206. A first rotor system 208 is coupled to an end of the first wing 204 and a second rotor system 210 is coupled to an end of the second wing 206. Each of the first and second rotor systems 208 and 210 of the illustrated example includes a rotatable engine 212. Each engine 212 includes a rotor 214 supporting rotor blades 216 and a nacelle 218 to house components of the engine 212 (e.g., a compressors, combustion chamber, nozzle, etc.). The engines 212 of the illustrated example include engine inlets 220 that receive high velocity airflow from the rotors 214. The engine inlets 220 of the illustrated example define openings provided by the nacelles 218, which provide certain flow characteristic(s) or profile(s) (e.g., laminar flow) to the engines 212.

In operation, the engines 212 of the first and second rotor systems 208 and 210 are selectively rotated between a helicopter mode and an airplane mode. In helicopter mode, the engines 212 are rotated to an approximately vertical position so that the aircraft 100 can perform vertical take-off, landing and hover in the air similar to a conventional helicopter. In airplane mode, the engines 212 are rotated to an approximate horizontally position so that the aircraft 100 can fly similar to a fixed wing aircraft (e.g., enable flight at higher speeds and/or greater distances like the fixed-wing aircraft).

During vertical hover, liftoff and/or takeoff, the rotor blades 216 pump a relatively large volume of air at a high velocity toward the engine inlets 220. Also, thrust generated by the example engines 212 is directed toward a ground surface 222 (e.g., sandy ground, a body of water, a ice/snow covered area, etc.). As a result of the engine orientation during vertical hover, liftoff and/or takeoff, the engines 212 produce a downwash effect that causes reduced visibility conditions (e.g., a brownout or whiteout condition) when the aircraft 100 is within a certain height from the ground surface 222 (e.g., between approximately 50 and 100 feet from the ground surface 222). For example, the downwash effect may create a brownout condition by agitating particulate on the ground surface 222 (e.g., dirt, sand, moisture, water, snow, ice, etc.) and causing the particulate (e.g., a dust cloud) to rise above the rotors 214, which draw (e.g., suck) the particulate and dirt toward the inlets 220 of the engines 212. For example, during descent and/or when the aircraft 100 hovers vertically, the engines 212 are susceptible to ingest particulate (e.g., sand) due to the rotors 214 being oriented skyward (e.g., as shown in the orientation of FIG. 1). In some such instances, the particulate is recirculated or entrained in a high velocity airflow generated by the rotors 214 and is directed toward the engine inlets 220 of the engines 212 at a relatively high velocity. Such high velocity particulate can cause deformation (e.g., erosion or damage) to the aircraft surfaces 104 (e.g., the rotor blades 216 or the engine inlets 220) of the aircraft 100. In some examples, the particulate or dirt can accrete on surfaces defining the engine inlets 220, which can affect airflow characteristic(s) to the engines 212. In some instances, surface deformation of the engine inlets 220 may degrade, damage and/or reduce engine efficiency. For example, surface deformation at the engine inlets 220 may cause varying airflow patterns to the engines 212, which may reduce engine efficiency and/or may cause engine flameout or compressor stall. In some instances, surface deformation of the rotor blades 216 may cause degradation to the expected lift at a given rotor speed (Nr).

Figure 3:
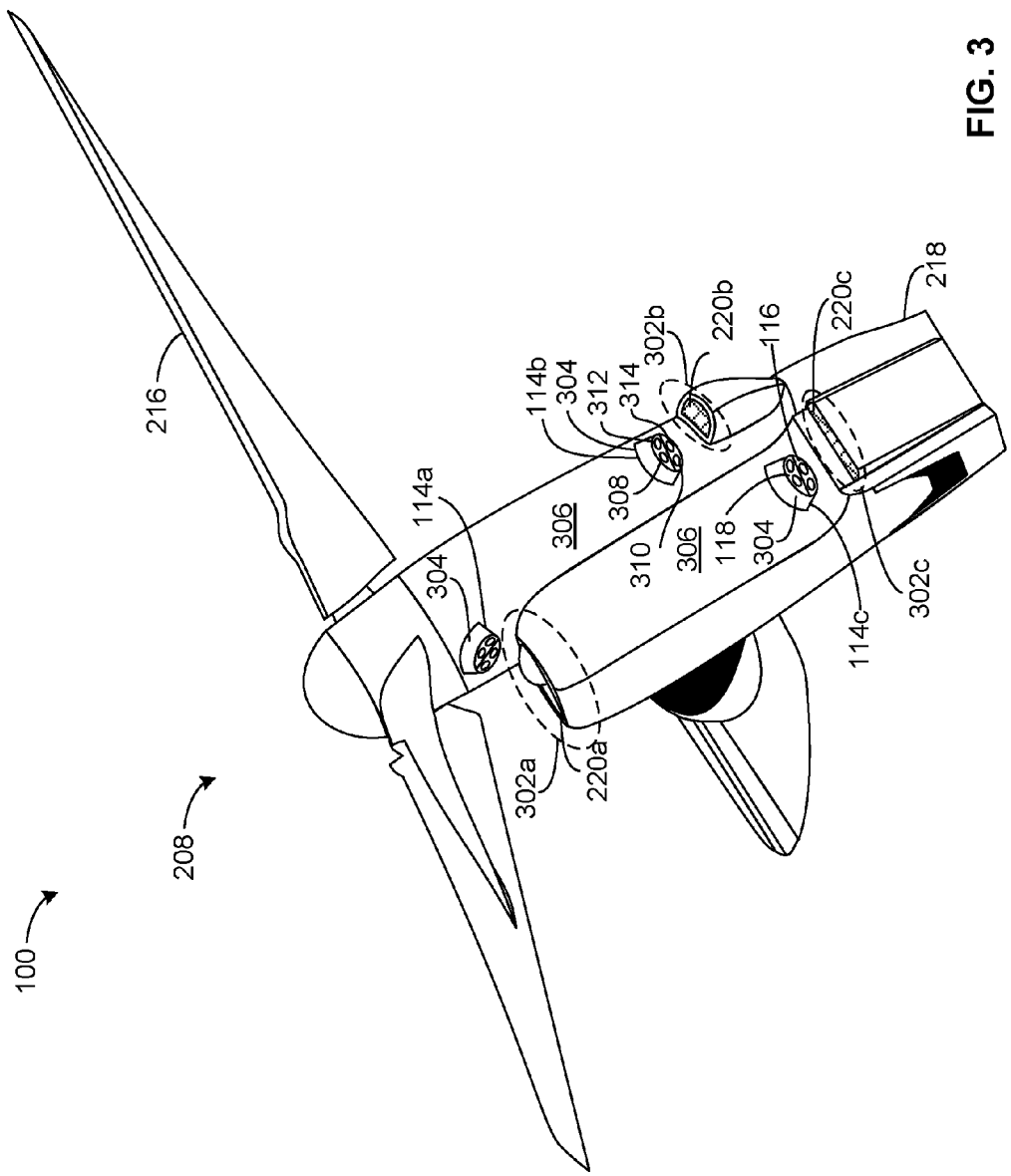
FIG. 3 is a partial, enlarged view of the example aircraft of FIGS. 1 and 2.

FIG. 3 is an enlarged view of the example first rotor system 208 of FIG. 2. The second rotor system 210 of FIG. 2 is substantially similar or identical to the example first rotor system 208 and in the interest of brevity, only the first rotor system 208 will be discussed in detail. However, one of ordinary skill in the art will understand that the structure and function of second rotor system 210 will be fully known from the benefit of the disclosure herein related to first rotor system 208.

In the illustrated example, the sensors 114 include a first sensor 114a to monitor a first point cloud 302a defining a first engine inlet 220a, a second sensor 114b to monitor a second point cloud 302b defining a second engine inlet 220b, and a third sensor 114c to monitor a third point cloud 302c defining a third engine inlet 220c. However, in some examples, the sensors (e.g., the sensors 114 of FIG. 1) may be positioned or directed to analyze the rotor blades 216 of the rotor 214, the wings 204, 206, the fuselage 202 and/or any other aircraft surface(s).

Each of the sensors 114a-c of the illustrated example includes a housing 304 (e.g., a sensor pod or Radome) coupled to the nacelle 218. For example, the housings 304 of the illustrated example may be mounted within respective openings formed in the nacelle 218 upstream from the respective engine inlets 220a-c associated with the respective one of the sensors 114a-c. In the illustrated example, the housing 304 protrudes from the nacelle 218. In some examples, a cover (e.g., a transparent cover) may be positioned over the sensors 114a-c. In some examples, the sensors 114a-c of the illustrated example may be flush mounted relative to an outer surface 306 (e.g., an aerodynamic surface) of the nacelle 218. For example, the sensors 114a-c may be substantially flush with and/or defines the outer surface 306 of the nacelle 218 such that the sensors 114a-c do not interfere, disrupt, modify and/or obstruct (e.g., a pattern or profile of) an airflow moving towards the inlets 220a-c of the engines 212.

As noted above in connection with FIG. 1, each of the sensors 114a-c of the illustrated example includes the first sensor 116 and the second sensor 118. The example first sensor 116 of the illustrated example is a laser sensor or transceiver (e.g., a Light Detection And Ranging (LIDAR) sensor). For example, the first sensors 116 of the illustrated example include a laser transmitter 308 and a receiver 310. The second sensor 118 of the illustrated example is an infrared sensor. For example, the second sensors 118 of the illustrated example include a transmitter 312 (e.g., a light emitting diode, an infrared or radiation emitter) and a receiver 314 (e.g., photodiode). The first sensor 116 and the second sensor 118 of the first sensor 114a are configured or positioned (e.g., aimed) to monitor the first point cloud 302a of the first engine inlet 220a. The first and second sensors 116 and 118 of the second sensor 114b are configured or positioned (e.g., aimed) to monitor the second point cloud 302b of the second engine inlet 220b, and the first and second sensors 116 and 118 of the third sensor 114c are configured or positioned (e.g., aimed) to monitor the third point cloud 302c of the third engine inlet 220c. The signals received by the receivers 310 and 314 are transmitted to the surface monitoring system 102.

Figure 4:
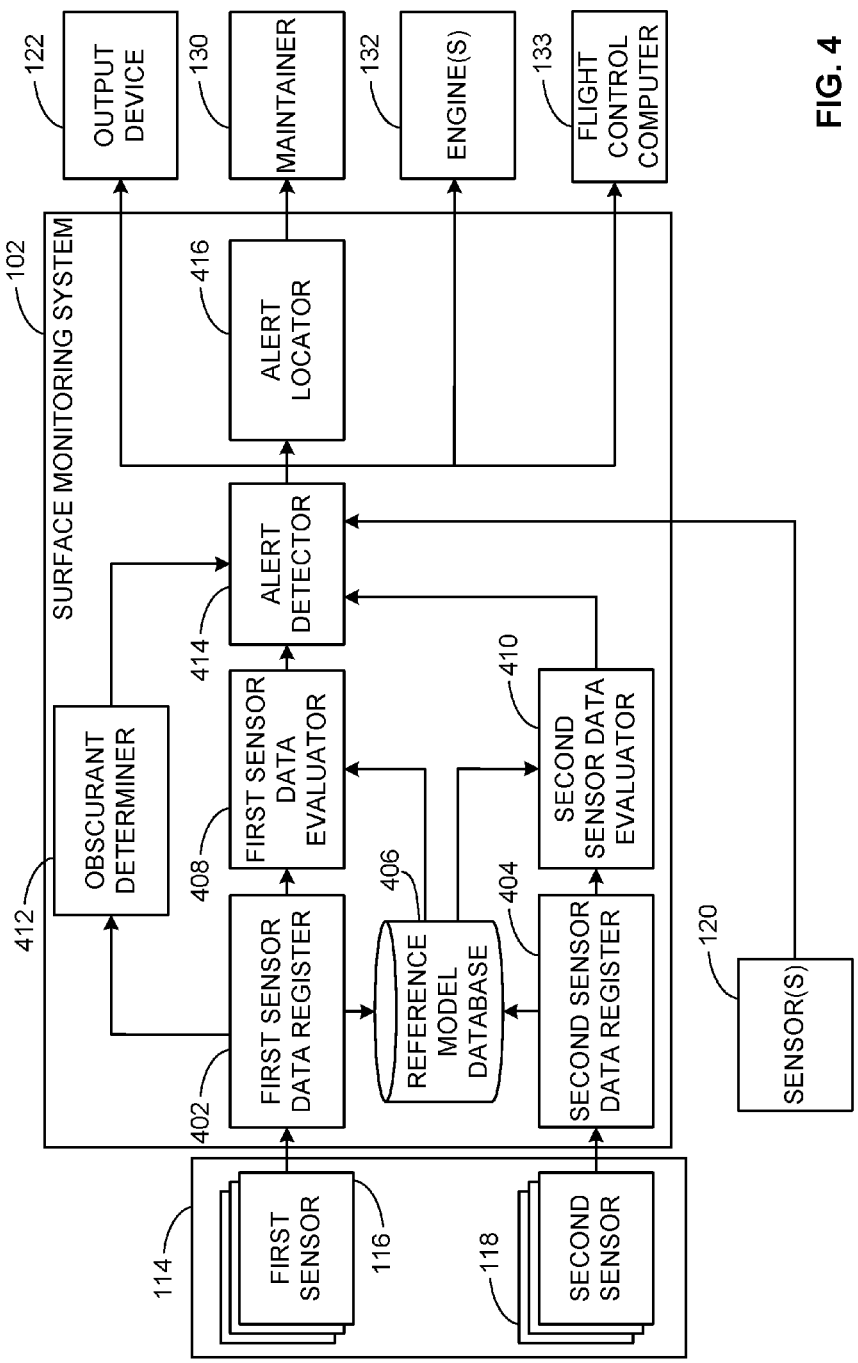
FIG. 4 is a block diagram of an example surface monitoring system of FIGS. 1-3.

FIG. 4 is a block diagram of the example surface monitoring system 102 disclosed herein. Referring to FIG. 4, the example surface monitoring system 102 includes an example first sensor data register 402, an example second sensor data register 404, an example reference model database 406, an example first sensor data evaluator 408, an example second sensor data evaluator 410, an example obscurant determiner 412, an example alert detector 414, and an example alert locator 416.

The first sensor data register 402 receives signals from the first sensor 116 of a respective one of the sensors 114. In some examples, when multiple sensors 114 are monitoring multiple aircraft surfaces 104, the first sensor data register 402 may include a signal identifier to determine a first sensor from which a signal is received by the first sensor data register 402. For example, an example signal identifier may determine or identify (e.g., tag) whether a signal received is provided by the example first sensor 116 associated with (i.e., monitoring) the engine inlet 106, the first sensor 116 associated with (i.e., monitoring) the control surface 108, the first sensor 116 associated with (i.e., monitoring) the aerodynamic surface 110, and/or the first sensors 116 associated with the (i.e., monitoring) the respective ones of the engine inlets 220a-c. In some examples, the surface monitoring system 102 may be configured to include a dedicated first sensor data register 402 for each first sensor 116 of the sensor system 112.

For example, laser energy (e.g., radiation, one or more wavelengths, etc.) emitted by the laser transmitter 308 of the first sensor 116 is directed to a point cloud defining one of the aircraft surfaces 104 (e.g., the first point cloud 302a of the engine inlet 220a). For example, the laser energy is reflected and/or backscattered and received by the receiver 310 of the first sensor 116, which transmits a corresponding signal to the first sensor data register 402. For example, the laser energy may be reflected or backscattered from the respective aircraft surface 104 (e.g., the engine inlet 106), an air cloud (e.g., from an intersection with particulate, liquid droplets in the air, etc.), an aerosol, etc. In some examples the first sensor data register 402 may include a clock or timer to determine a time differential between two or more signals (e.g., a time differential between two or more signals generated from the backscattered laser energy received by the first sensor data register 402).

More specifically, the first sensor data register 402 converts or conditions the backscattered laser energy signals (e.g., raw data, data representative of a wavelength, changes in wavelength, etc.) to generate computer processable electronic signals that may be analyzed to detect or determine surface deformation, identify particulate information (e.g., determine density), determine obscurant measurements, and/or determine other environmental conditions or flight parameters. For example, the backscattered energy signals such as, for example, wavelengths, polarized wavelengths, intensity of the backscattered energy, an angle an which the backscattered energy is detected, and/or any other analysis of backscattered energy may be used to provide information or data representative of a surface profile or condition (e.g., of the aircraft surfaces 104), surface deformation, environmental conditions, operating parameters, obscurant conditions and/or any other data.

Additionally, the first sensor data register 402 provides data representing an initial or reference model of the aircraft surface 104 (e.g., the engine inlet 220a) that the first sensor 116 is monitoring and stores the information in the reference model database 406. For example, the reference model of the aircraft surface 104 may be determined at start-up of the aircraft 100. In some examples, the first sensor data register 402 generates or captures an image at an initial stage of a flight (e.g., prior to take-off). In some examples, the first sensor data register 402 generates data points of a point cloud (e.g., the first point cloud 302a) representative of the aircraft surface 104 being monitored by the first sensor 116 at an initial stage of a flight (e.g., prior to take-off). Thus, the reference model of the aircraft surface 104 may be representative of a non-deformed (e.g., an ideal) surface condition of the aircraft surface 104 determined prior to a flight. In some examples, the reference model may be determined during manufacture of the aircraft 100 and the reference model may be stored in the reference model database 406.

The first sensor data register 402 of the illustrated example communicates the processed electronic signals to the first sensor data evaluator 408. As described in greater detail in connection with FIG. 5, the first sensor data evaluator 408 of the illustrated example detects surface deformation, environmental characteristic(s) and/or operating parameters and communicates the information to the alert detector 414. For example, to determine surface deformation, air data and/or environmental condition(s), the first sensor data evaluator 408 may employ different LIDAR modes or scattering techniques including, for example, Rayleigh scattering, Mie Scattering, Raman Scattering, full wave processing, polarization, and/or any other suitable scattering. In some examples, the first sensor data evaluator 408 may analyze an intensity of the backscattered energy and/or polarization to determine a change (e.g., an accretion of material) to the aircraft surface 104 and/or detect environmental condition(s).

In the illustrated example, the first sensor data register 402 provides information (computer processable data) to the obscurant determiner 412. The obscurant determiner 412 uses the data associated with the backscattered energy measured by the first sensor 116 to determine obscurant conditions surrounding the aircraft 100. For example, the obscurant determiner 412 of the illustrated example determines if the aircraft is exposed to rain, fog, rotor induced dust cloud, icy conditions, sand and/or any other obscurant(s). The obscurant determiner communicates obscurant measurements to the alert detector 414.

The second sensor data register 404 receives signals from the second sensor 118 of a respective one of the sensors 114. In some examples, the second sensor data register 404 may include a signal identifier to determine a second sensor from which a signal is received by the second sensor data register 404. For example, an example signal identifier may determine or identify (e.g., tag) whether a signal received is provided by the example second sensor 118 associated with (i.e., monitoring) the engine inlet 106, the second sensor 118 associated with (i.e., monitoring) the control surface 108, the second sensor 118 associated with (i.e., monitoring) the aerodynamic surface 110, and/or the second sensors 118 associated with the (i.e., monitoring) the respective ones of the engine inlets 220a-c. In some examples, the surface monitoring system 102 of the illustrated example includes a dedicated second sensor data register 404 for each second sensor 118 of the sensor system 112.

In the illustrated example, infrared energy (e.g., radiation in the infrared spectrum.) emitted by the transmitter 312 of the second sensor 118 is directed to a point cloud defining the aircraft surface 104 (e.g., the first point cloud 302a of the engine inlet 220a). In some examples, the infrared sensor may include optical components to focus or direct the infrared signal to the point cloud associated with the aircraft surface 104. The transmitter 312 emits infrared radiation directed toward the point cloud of the aircraft surface 104 (e.g., the engine inlet 106) and the receiver 314 receives the reflected signal to determine an object shape and/or a thermal profile of surfaces defining the engine inlets 220. For example, the infrared energy is reflected and received by the receiver 314 of the second sensor 118, which transmits a corresponding signal to the second sensor data register 404. For example, the infrared energy may be reflected from the respective aircraft surface 104 (e.g., the engine inlet 106). In some examples the first sensor data register 402 may include a clock or timer to determine a time differential between two or more signals (e.g., a time differential between two or more signals generated from the backscattered laser energy received by the second sensor data register 404).

The second sensor data register 404 converts or conditions the reflected infrared energy signals to computer processable electronic signals or data that may be analyzed to detect or determine surface deformation, a thermal profile of the aircraft surface 104 and/or other environmental conditions or flight parameters. Additionally, the second sensor data register 404 provides data representing an initial or a base reference model (e.g., an optimal model) of the aircraft surface 104 (e.g., the engine inlet 220a) that the second sensor 118 is monitoring and stores the information in the reference model database 406. For example, the reference model of the aircraft surface 104 may be determined at start-up of the aircraft 100. For example, the second sensor data register 404 generates or captures an image or data points of a point cloud (e.g., the first point cloud 302a) representative of the aircraft surface 104 being monitored by the second sensor 118 at an initial stage of a flight mission (e.g., prior to take-off). Thus, the reference model of the aircraft surface 104 may be representative of a non-deformed (e.g., an ideal) surface condition of the aircraft surface 104 determined prior to a flight. In some examples, the reference model may be determined during manufacture of the aircraft 100 and the reference model may be stored in the reference model database 406.

The second sensor data register 404 of the illustrated example communicates the processed electronic signals to the second sensor data evaluator 410. The second sensor data evaluator 410 of the illustrated example detects surface deformation, generates a thermal profile of the aircraft surface 104 and/or may determine environmental characteristic(s) and/or operating parameters. For example, second sensor data evaluator 410 generates a plurality of current images or data points of a point cloud (e.g., the first point cloud 302a) representative of the aircraft surface 104 being monitored by the second sensor 118 during a flight mission (e.g., every several milliseconds during flight). To detect deformation, the second sensor data evaluator 410 compares the current data points of the point cloud during a mission with the initial or reference data points of the point cloud obtained prior to the mission flight. In some examples, the second sensor data evaluator 410 detects a change in a detected surface deformation by comparing the data points of the point cloud obtained during a flight over a period of time. Thus, the second sensor data evaluator 410 of the illustrated example can detect accretion of material over a period of time. The second sensor data evaluator 410 communicates the information to the alert detector 414.

The alert detector 414 of the illustrated example receives the surface deformation information, aircraft operating parameter(s) and/or environmental condition(s) information from the first sensor data evaluator 408 and the second sensor data evaluator 410, the obscurant measurement information from the obscurant determiner 412, and/or aircraft operating parameter(s) and air data characteristic(s) from the aircraft sensors 120. As described in greater detail below in connection with FIG. 6, the example alert detector 414 of the illustrated example determines whether aircraft operating condition(s) and/or environmental flight conditions affect aircraft performance in view of a detected surface deformation provided by the first sensor data evaluator 408 and/or the second sensor data evaluator 410. In some examples, the example alert detector 414 disclosed herein may determine or classify a severity of a detected surface deformation in view of one or more parameters (e.g., surface deformation characteristic(s), environmental data, aircraft state or operating parameters, etc.) to determine the likelihood of the detected surface deformation impacting aircraft performance and/or safety.

The alert detector 414 communicates an alert or alarm to the output device 122 of the aircraft 100, the maintainer 130 and/or an electronic engine controller of the engine(s) 132 and/or flight control computer 133. In some examples, the surface monitoring system 102 of the illustrated example may include an alert locator 416 to detect a location of a detected surface deformation. For example, the alert locator 416 may determine or identify the aircraft surfaces 104 with a detected surface deformation and communicates the identified aircraft surfaces 104 to the maintainer 130.

Figure 5:
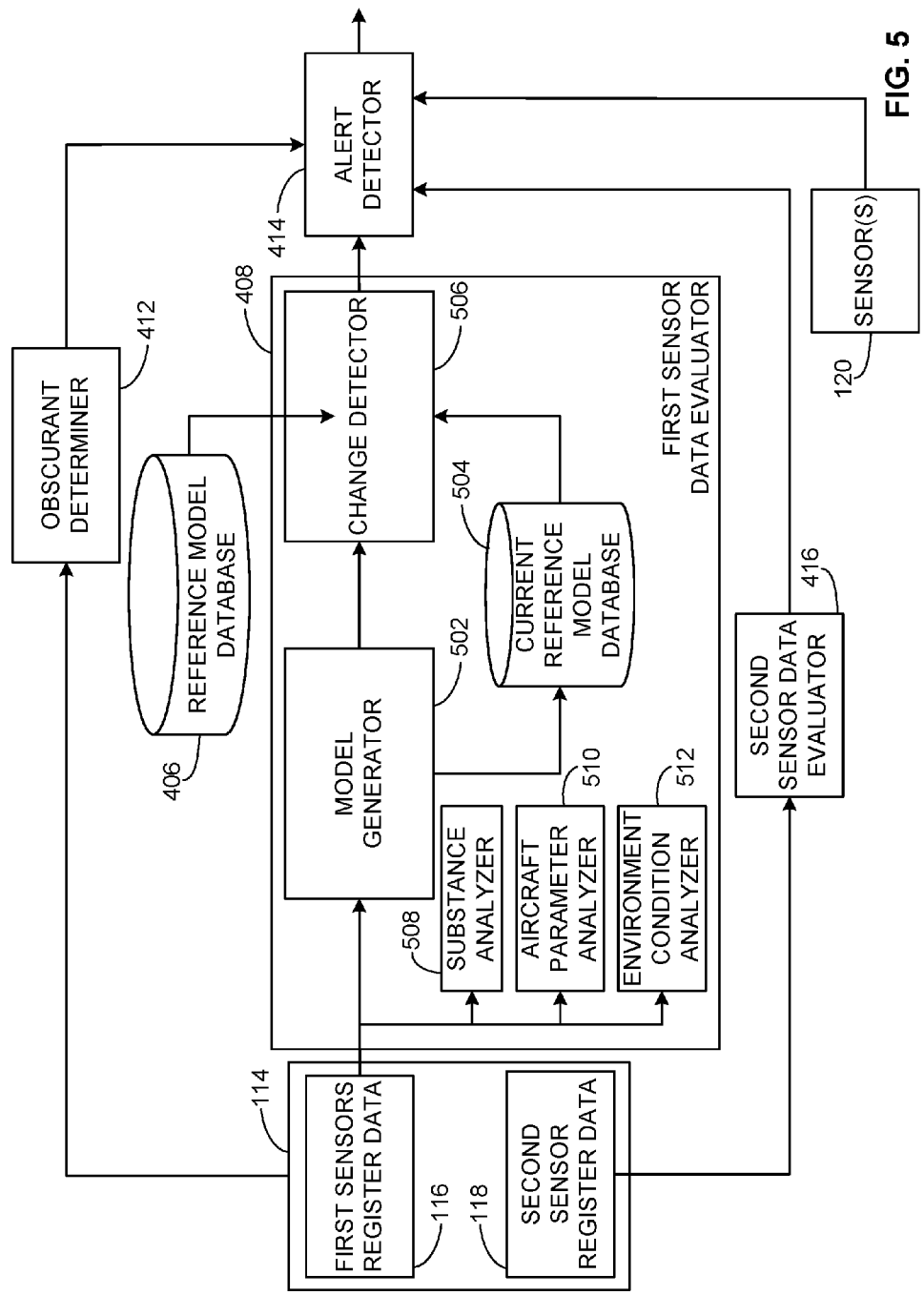
FIG. 5 is a block diagram of an example first sensor data evaluator of the example surface monitoring system of FIGS. 1-4.

FIG. 5 is a block diagram of the example first sensor data evaluator 408 of FIG. 4. The first sensor data evaluator 408 of the illustrated example includes an example model generator 502, an example current reference model database 504, an example change detector 506, an example substance analyzer 508, an example aircraft parameter analyzer 510, and an environmental condition analyzer 512.

The example model generator 502 of the illustrated example receives data or information from the first sensor data register 402 and generates or determines (e.g., builds) a current reference profile of the monitored aircraft surface 104. For example, the first sensor data evaluator 408 of the illustrated example processes the data from the first sensor data register 402 using algorithms to determine a surface profile of the aircraft surface 104 being monitored by the first sensor 116. In some examples, the model generator includes a timer to time stamp each detected current reference model generated by the model generator 502.

The model generator 502 communicates the current reference model and stores the information in a current model reference model database (e.g., memory). The current reference model may be an image, data points of a point cloud representative of surface contours provided in tabular form, and/or any other data. For example, the model generator 502 establishes an image or data points (e.g., x-axis, y-axis, a z-axis coordinates) representative of a point cloud of the aircraft surface 104. For example, the point cloud is a set of data points defined by x, y, and z coordinates that represent external surface (e.g., contours, profile, or shape) of the aircraft surface 104. For example, the point cloud may measure or model contours or shapes of the aircraft surfaces.

The first sensor data evaluator 408 samples or generates a plurality of current model references (e.g., images or data points) of a point cloud (e.g., the first point cloud 302a) during a flight (e.g., every several milliseconds during flight). As noted above, the model generator 502 may be configured to time stamp each current reference model generated during the flight mission. The model generator 502 stores current reference models in the current reference model database 504.

In turn, the change detector 506 processes the information from the model generator 502 to determine deformation of the aircraft surface 104 and communicates the information to the alert detector 414. For example, the change detector 506 retrieves the current reference model from the current reference model database 504 and the base reference model from the reference model database 406. In particular, the change detector 506 compares, via a comparator, the current reference model and the base reference model to detect surface deformation in the aircraft surface 104 monitored by the first sensor 116. For example, if the images and/or the data points differ by, for example a threshold (e.g., some combination of parameters that when converted to a mathematical value by a weighted polynomial that exceeds a predetermined value) between the base reference model and the current reference model, the change detector 506 detects surface deformation of the aircraft surface 104. In some examples, the change detector 506 of the illustrated example compares or samples a plurality of current reference models (e.g. obtained over time) to detect changes in the surface deformation of the aircraft surface 104. For example, the change detector 506 detects a change in a detected surface deformation by comparing data points of the point cloud obtained during a flight over a period of time. For example, the change detector 506 of the illustrated example can detect or quantify an accretion of material on the aircraft surface 104 over a period of time as well as a rate of accumulation that can be used to trigger a notification to the crew.

In some examples, the change detector 506 of the illustrated example, based on the comparison between the current reference model and the base reference model and/or a first current reference model and a second current reference model, can determine characteristics of the surface deformation. For example, the change detector 506 can detect a change in intensity of backscattered energy (e.g., a change greater than a threshold) to determine accretion of material on the aircraft surface 104. For example, a backscattered energy having a greater intensity is indicative of a clean surface (e.g., the absence of particulate) compared to an intensity level of backscattered energy reflected off particulate accreted on the aircraft surface 104. In some examples, the change detector 506 of the illustrated example compares the change in the aircraft surface 104 detected by the first sensor data evaluator 408 and the second sensor data evaluator 410 to determine a dimensional characteristic (e.g., a height or shape) of the accreted material on the monitored aircraft surface 104. For example, the change detector 506 compares a thickness value, a thickness, a height, a shape, an area, a perimeter and/or other dimensional or profile characteristic(s) of the accreted material or surface deformation (e.g., a crack, hole or concave shape).

Additionally, in some examples, the substance analyzer 508, the aircraft parameter analyzer 510 and/or the environmental condition analyzer 512 receives electronic signals from the first sensor data register 402 to determine characteristic(s) of foreign substances on the aircraft surface 104 and/or one or more air data and/or environmental characteristic(s). For example, the first sensor data evaluator 408 may process the electronic signals from the first sensor data register 402 using weighted polynomials (e.g., Equations 1-4 noted below) to detect foreign material characteristic(s) (e.g., density, type, etc.), air data and/or operating parameters and/or their relative values when compared to, for example, predefined values that correspond to loss or degraded engine power or aerodynamic properties. For example, the first sensor data evaluator 408 detects intensity or polarization characteristics of the backscattered energy to determine foreign material characteristic(s) (e.g., density or material type), flight conditions and/or environmental conditions around the aircraft 100.

In some examples, one or more characteristics (e.g., pressure, temperature, density) of the air and/or an accreted material on the monitored aircraft surface 104 may be determined by comparing (e.g., matching) the electronic signals converted by the first sensor data register 402 (and/or the second sensor data register 404) to experimentally determined values associated with materials and/or air characteristics (e.g., density, pressure, temperature, particle size, etc.). For example, the first sensor data evaluator 408 may retrieve stored information from a look-up table to compare, via a comparator, the electronic signals provided by the first sensor data register 402 with stored values in a look-up table to determine pressure, temperature, velocity and/or density of the air, density of accreted material(s) on the aircraft surface 104 and/or any other information.

For example, the change detector 506 determines a characteristic(s) (e.g., a density, type of material(s), a volume of material, etc.) accreting on the aircraft surface 104 by analyzing a wavelength of the detected backscattered laser energy and/or a measured size (e.g., a diameter) of a material particle detected by the backscattered laser energy. For example, the aircraft parameter analyzer 510 may process the electronic signals or data using algorithms applying Doppler velocity to determine air speed and/or velocity from a frequency shift analysis. For example, the environmental condition analyzer 512 analyzes a wavelength graph (e.g., a line thickness, a magnitude, etc.) and/or measure an intensity of the detected backscattered laser energy to determine a pressure and/or a temperature of the air surrounding the aircraft 100. For example, the environmental condition analyzer 512 determines a particulate density based on backscattered laser energy.

The second sensor data evaluator 410 may be implemented substantially similar to the example first sensor data evaluator 408 and, thus, the second sensor data evaluator 410 will not be discussed. For example, the second sensor data evaluator 410 of the illustrated example may include a model generator, a current reference model database and a change detector similar to the model generator 502, the current reference model database 504, and the change detector 506 of the first sensor data evaluator 408 to determine or detect characteristic(s) of the surface deformation of the aircraft surface 104. For example, the second sensor data evaluator 410 generates a plurality of current images or data points of a point cloud (e.g., the first point cloud 302a) representative of the aircraft surface 104 being monitored by the second sensor 118 during a flight mission (e.g., every several milliseconds during flight). To detect deformation, the second sensor data evaluator 410 compares the current data points of the point cloud obtained during a flight with the initial or reference data points of the point cloud obtained prior to the flight. In some examples, the second sensor data evaluator 410 detects a change in a detected surface deformation by comparing the data points of the point cloud obtained during a mission over a period of time. Thus, the second sensor data evaluator 410 of the illustrated example can detect accretion of material over a period of time. In some examples, the second sensor data evaluator 410 may detect, for example, a thickness of the surface deformation (e.g., a thickness of the accretion), a shape of the surface deformation, a density of material causing the surface deformation, a temperature gradient of the surface deformation and/or other data relating to the surface deformation.

Figure 6:
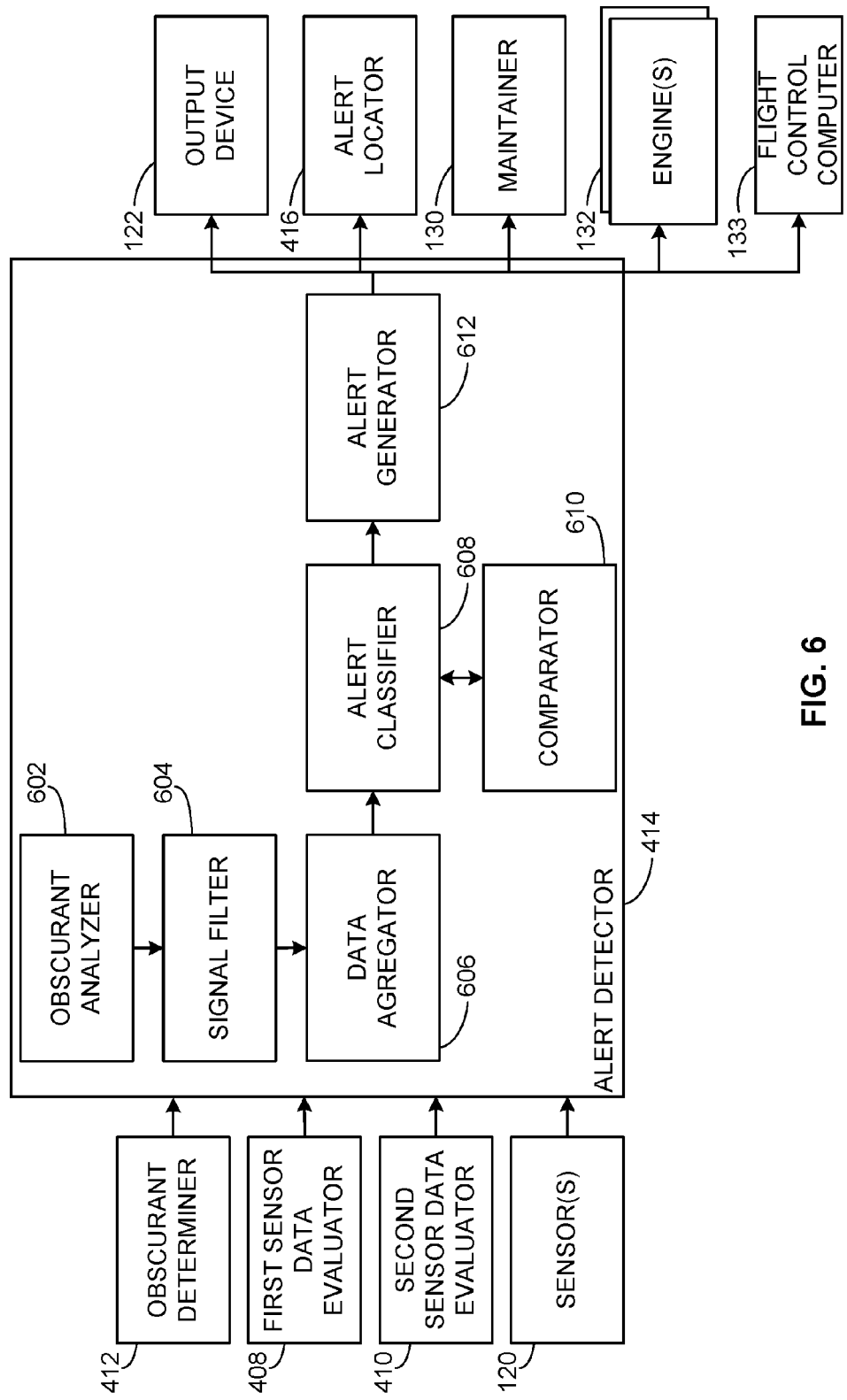
FIG. 6 is a block diagram of an example alert detector of the example surface monitoring system of FIGS. 1-5.

FIG. 6 is a block diagram of the example alert detector 414 of FIGS. 4 and 5. The example alert detector 414 of the illustrated example includes an example obscurant analyzer 602, an example signal filter 604, an example data aggregator 606, an example alert classifier 608, an example comparator 610 and an example alert generator 612.

As noted above, the example alert detector 414 receives aircraft surface deformation information from the first sensor data evaluator 408 and the second sensor data evaluator 410, operating parameters (e.g., airspeed, altitude, etc.) and environmental conditions (e.g., humidity, air pressure, air temperature, humidity, air density, etc.) from the first sensor data evaluator 408, the second sensor data evaluator 410 and/or the aircraft sensors 120, and the obscurant measurement information from the obscurant determiner 412.

The obscurant analyzer 602 determines if the obscurant measurement may affect accuracy of the first sensor 116 and/or the second sensor 118. For example, the obscurant analyzer 602 compares the obscurant measurement to a threshold value to determine if the obscurant conditions affect reliability of the sensor system 112. The obscurant analyzer 602 communicates the information to the signal filter 604.

The signal filter 604 of the illustrated example discriminates signals from certain sensors that may provide inferior signaling during obscurant conditions. For example, the signal filter 604 ignores signals from certain ones of the sensors 114 if the obscurant analyzer 602 determines that the obscurant measurement is greater than the threshold. For example, the signal filter 604 may ignore signals or detections from the second sensor 118 (e.g., an infrared signal) and/or the second sensor data evaluator 410 when certain obscurant conditions are present and will process only information based on the signals received from the first sensor 116 (e.g., a LIDAR sensor).

The data aggregator 606 receives the aircraft surface deformation information, the operating parameters, the environmental conditions, and the obscurant measurement information from the signal filter 604. The alert classifier analyzes (e.g., via algorithms) the surface deformation information, the operating parameter information, the environmental condition information, and/or the obscurant measurement analyzer to determine a severity of a hazard presented by the detected surface deformation and the likelihood of the operating parameters and/or the environmental conditions impacting aircraft performance or safety. For example, the data aggregator 606 analyzes one or more of air pressure, air temperature, altitude, air density, a thickness of a foreign matter accreted on the aircraft surface, a shape of the foreign matter, a density of the foreign matter, a temperature gradient or profile of the aircraft surface, and/or any other information regarding the foreign matter, environmental conditions, operating parameters, and/or obscurant conditions.

To determine a severity of a hazard condition, the example data aggregator 606 of the illustrated example determines a scaled value based on the information provided by the signal filter 604. In some examples, the data aggregator 606 determines the scaled value by analyzing the surface deformation information, the environmental conditions, and/or the operating parameters. For example, the data aggregator 606 generates a scaled value by assigning different weighted values to the different environmental conditions (e.g., air pressure, air temperature, humidity, air density, etc.), operating parameters (e.g., airspeed, altitude, angle of attack, etc.) and/or surface deformation (e.g., density of foreign material, volume, density, area of a foreign material, an area of an opening formed in the aircraft surface, etc.) and/or other parameters. For example, the data aggregator 606 weights the different parameters and employs an algorithm (e.g., a polynomial equation) to determine the scaled value. For example, air temperature, surface temperature, density, dimensional characteristic(s) of the surface deformation may be weighted greater than, for example, air pressure, airspeed, etc. The scaled value is communicated to the alert classifier 608.

For example, a scaled value may be determined by the data aggregator 606 from the following equations.

For example, a deformation at a point n at time t may be determined by Equation 1:

$$D_{n(t)} = w_1 t_h + w_2 d + w_3 r + w_4 t_e + \ldots + w_x p_x \qquad \text{Eq. 1:}$$

where $t_h$ is a thickness of the point n at time t; d is a density of a material at point n at time t; $t_e$ is a temperature of point n at time t; $P_x$ is any other parameter that may be used to determine the deformation at point n; $w_1$, $W_2$, $W_3$, $W_4$, $w_x$ are constant weighting factors associated with the respective physical parameters $t_h$, d, $t_e$, $p_x$, respectively.

In some examples, a total deformation at time t may be determined by a summation of the deformations at different points n (e.g., of a point cloud) using Equation 2:

$$D_{total} = \Sigma_{n=1}^{n=end} D_{n(t)} \qquad \text{Eq. 2:}$$

In some examples, a rate of deformation may be determined to infer an impending change to aerodynamic performance. A rate of deformation may be determined using Equation 3:

$$\dot{D} = \frac{dD_{total}}{d_t} \qquad \text{Eq. 3}$$

Alternatively, in some examples, a method for determining disruption to air flow over an aircraft surface 104 (e.g., aerodynamic surface or engine inlet) may be determined by the sum of all deformations representing a surface (S) (e.g., aircraft surface 104 or a point cloud, surface points $S_0$ to $S_n$) integrated over that space or surface as compared to the surface area from the reference model. For example, Equation 4 may be used to determine disruption to air flow over an aerodynamic surface:

$$\oiint_{S0}^{Sn} f(x,y,z) dS \qquad \text{Eq. 4:}$$

Alternatively, in some examples, the data aggregator 606 compares two or more environmental conditions and/or the operating parameters to determine a severity of a detected surface deformation. For example, if air temperature and/or a surface temperature of the aircraft surface 104 is greater than a threshold temperature and an airspeed of the aircraft is less than an airspeed threshold, the example data aggregator 606 may determine that a surface deformation is severe. For example, the data aggregator 606 may determine that a detected surface deformation may not be severe when a dimensional characteristic of foreign matter accreting on the aircraft surface 104 is not increasing over a sample time period and an air temperature is below a threshold temperature, a density of the foreign matter is below a threshold density, and/or any other parameter is below or within a desired range. In some examples, the data aggregator 606 may determine surface deformation severity is increasing when a dimensional characteristic of foreign matter accreting on the aircraft surface 104 is increasing over a sample time period and an air temperature is below a threshold temperature, a density of the foreign matter is below a threshold density, a surface temperature of the aircraft surface is below a threshold, and/or any other parameter is below or within a desired threshold range. In some examples, the data aggregator 606 may determine that a surface deformation is severe when a dimensional characteristic of foreign matter accreting on the aircraft surface 104 is increasing over a sample time period and an air temperature is greater than a threshold temperature, a density of the foreign matter is greater than a threshold density, a surface temperature of the aircraft surface is greater than a threshold, and/or any other parameter is greater than a desired threshold range. For example, when surface deformation is caused by accretion of sand and the air temperature and/or the aircraft surface temperature is relative high (e.g., greater than a threshold), the sand can melt and create a change in the airflow due to turbine blade glassification, thereby reducing the efficiency of the aircraft 100. Thus, the data aggregator 606 may generate a warning based on these two parameters. In some examples, these two parameters are awarded a greater weight when determining the scaled value.

The alert classifier 608 determines or classifies a level of severity of the detected surface deformation based on the inputs analyzed by the data aggregator 606. For example, the levels of severity may include, for example, an advisory alert, a caution alert, and a warning alert. The advisory alert provides situational awareness such as, for example, a suggestion that surface deformation is commencing, the caution alert provides information that surface deformation is building on the aircraft surface, and the warning alert provides awareness that deformation is impacting aircraft performance. To detect the level of severity, the alert classifier 608 of the illustrated example compares the scaled value provided by the data aggregator 606 to a threshold range. For example, the alert classifier 608 of the illustrated example initiates an advisory alert when the scaled value is less than a lower limit of the threshold range, initiates the warning alert when the scaled value is greater than an upper limit of the threshold range, and initiates a caution alert when the scaled value is within the threshold range.

The alert classifier 608 communicates the alert status to the alert generator 612. The alert generator 612 communicates the alert to the output device 122, the flight data recorder 128, the maintainer 130, and/or an electronic engine controller of the engine 132 and/or the flight control computer 133.

While an example manner of implementing the surface monitoring system 102 of FIG. 1 is illustrated in FIGS. 4-6, one or more of the elements, processes and/or devices illustrated in FIGS. 4-6 may be combined, divided, rearranged, omitted, eliminated and/or implemented in any other way. Further, the example first sensor data register 402, the example second sensor data register 404, the example reference model database 406, the example first sensor data evaluator 408, the example second sensor data evaluator 410, the example obscurant determiner 412, the example alert detector 414, the example alert locator 416, the example model generator 502, the example current reference model database 504, the example change detector 506, the example substance analyzer 508, the example aircraft parameter analyzer 510, the environmental condition analyzer 512, the example obscurant analyzer 602, the example signal filter 604, the example data aggregator 606, the example alert classifier 608, the example comparator 610 and the example warning generator 612 and/or, more generally, the example surface monitoring system of FIG. 1 may be implemented by hardware, software, firmware and/or any combination of hardware, software and/or firmware. Thus, for example, any of the example first sensor data register 402, the example second sensor data register 404, the example reference model database 406, the example first sensor data evaluator 408, the example second sensor data evaluator 410, the example obscurant determiner 412, the example alert detector 414, the example alert locator 416, the example model generator 502, the example current reference model database 504, the example change detector 506, the example substance analyzer 508, the example aircraft parameter analyzer 510, the environmental condition analyzer 512, the example obscurant analyzer 602, the example signal filter 604, the example data aggregator 606, the example alert classifier 608, the example comparator 610 and the example warning generator 612 and/or, more generally, the example surface monitoring system 102 of FIG. 1 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example first sensor data register 402, the example second sensor data register 404, the example reference model database 406, the example first sensor data evaluator 408, the example second sensor data evaluator 410, the example obscurant determiner 412, the example alert detector 414, the example alert locator 416, the example model generator 502, the example current reference model database 504, the example change detector 506, the example substance analyzer 508, the example aircraft parameter analyzer 510, the environmental condition analyzer 512, the example obscurant analyzer 602, the example signal filter 604, the example data aggregator 606, the example alert classifier 608, the example comparator 610 and the example warning generator 612 and/or, more generally, the example surface monitoring system of FIG. 1 are hereby expressly defined to include a tangible computer readable storage device or storage disk such as a memory, a digital versatile disk (DVD), a compact disk (CD), a Blu-ray disk, etc. storing the software and/or firmware. Further still, the example the example surface monitoring system of FIG. 1 may include one or more elements, processes and/or devices in addition to, or instead of, those illustrated in FIGS. 4-6, and/or may include more than one of any or all of the illustrated elements, processes and devices.

Figure 7:
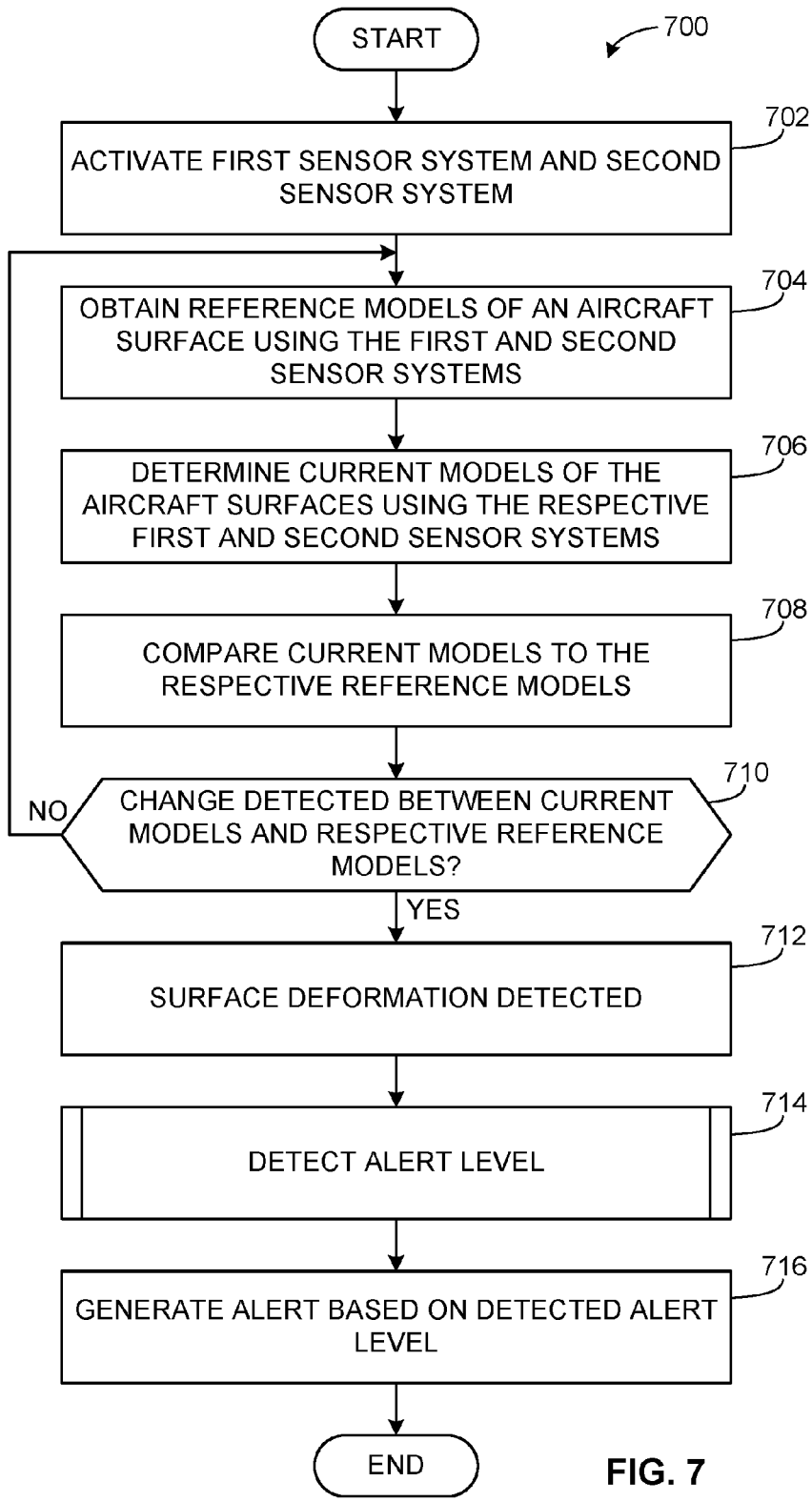
FIG. 7 is a flowchart representative of an example method that may be used to implement the example surface monitoring system of FIGS. 1-6.
Figure 8:
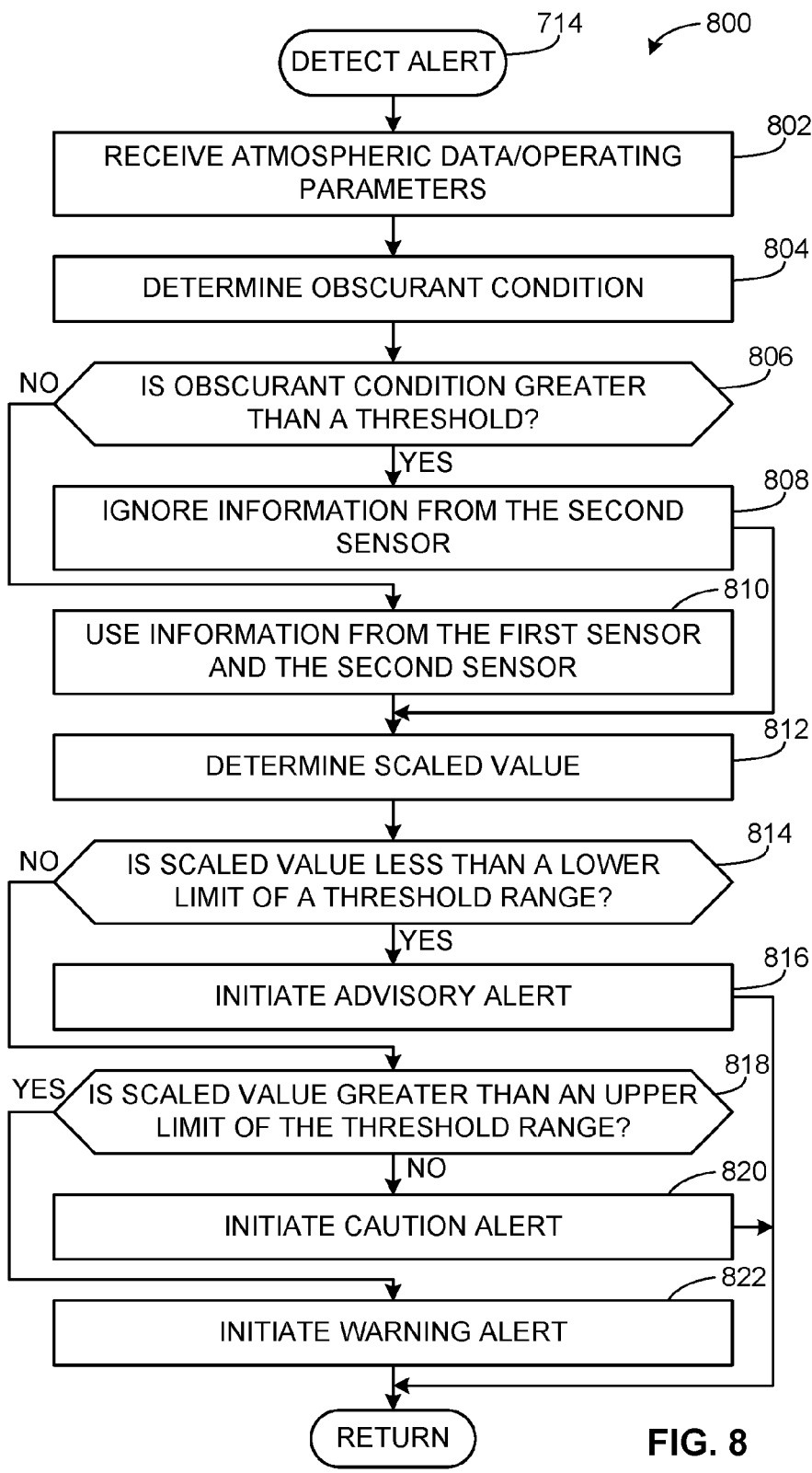
FIG. 8 is a flowchart representative of an example method to determine an alert level of the example surface monitoring system of FIGS. 1-7.

Flowcharts representative of example methods 700, 800 for implementing the example surface monitoring system 102 of FIG. 1 are shown in FIGS. 7 and 8. The methods may be implemented using machine readable instructions that comprise a program for execution by a processor such as the processor 912 shown in the example processor platform 900 discussed below in connection with FIG. 9. The program may be embodied in software stored on a tangible computer readable storage medium such as a CD-ROM, a floppy disk, a hard drive, a digital versatile disk (DVD), a Blu-ray disk, or a memory associated with the processor 912, but the entire program and/or parts thereof could alternatively be executed by a device other than the processor 912 and/or embodied in firmware or dedicated hardware. Further, although the example programs are described with reference to the flowcharts illustrated in FIGS. 7-8, many other methods of implementing the example surface monitoring system 102 may alternatively be used. For example, the order of execution of the blocks may be changed, and/or some of the blocks described may be changed, eliminated, or combined.

As mentioned above, the example methods 700, 800 of FIGS. 7-8 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example methods 700, 800 of FIGS. 7-8 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

The method 700 of FIG. 7 begins at block 702 when the surface monitoring system 102 activates the sensor system 112. For example, the surface monitoring system 102 activates the first sensor 116 and the second sensor 118 to monitor the aircraft surface 104 of the aircraft 100. The surface monitoring system 102 obtains a reference model of the aircraft surface 104 using the sensor system 112 (block 704). For example, the first sensor data register 402 generates a reference model based on signals received from the first sensor 116 and the second sensor data register 404 generates a reference model of the aircraft surfaces 104 based on the signals provided by the second sensor 118. During a flight mission, the surface monitoring system 102 generates current models of the aircraft surface 104 using the first sensor 116 and the second sensor 118 (block 706). For example, the model generator 502 receives information (e.g., data points) from the first sensor data register 402 to determine the current model of the aircraft surface 104. For example, the surface monitoring system 102 of the illustrated example may obtain a current model of the aircraft surface every several milliseconds. The change detector 506 compares, e.g., via a comparator, the current model of the aircraft surface and the reference model of the aircraft surface (block 708) to detect a change between the current model and the reference model (block 710). If the surface monitoring system 102 does not detect a change in the aircraft surface 104 at block 710, the surface monitoring system 102 returns to block 706. If the surface monitoring system 102 detects a change in the aircraft surface 104 at block 710, the surface monitoring system 102 determines that a surface deformation is detected (block 712). The alert detector 414 then detects or classifies an alert level (block 714). The alert detector 414 generates an alert based on the detected alert level (block 716).

FIG. 8 illustrates an example method 800 for detecting an alert level for implementing block 714 of FIG. 7. The method 800 of FIG. 8 begins when the alert detector 414 receives the environmental data and the operating parameters (block 802). For example, the data aggregator 606 receives environmental data and operating parameters from the first sensor data evaluator 408, the second sensor data evaluator 410 and/or the aircraft sensors 120. The data aggregator 606 also receives obscurant condition information from the obscurant determiner 412 (block 804).

The obscurant analyzer 602 determines if the obscurant condition is greater than a threshold (block 806). If the obscurant condition is greater than a threshold at block 806, the signal filter 604 ignores or filters the information (e.g., surface deformation information, environmental data and/or operating parameters) from the second sensor data evaluator 410 and/or the second sensor 118 (e.g., the infrared sensor) (block 808). In some such instances, the data aggregator 606 employs the data (e.g., surface deformation information, environmental data and/or operating parameters) from the first sensor data evaluator 408 and/or the first sensor 116.

If the obscurant condition is not greater than the threshold at block 806, the data aggregator 606 considers the information (e.g., surface deformation information, environmental data and/or operating parameters) from the first sensor data evaluator 408 (e.g., the first sensor 116) and/or the second sensor data evaluator 410 (e.g., the second sensor 118)(block 810).

The data aggregator 606 of the illustrated example determines a scaled value (block 612). In some examples, the data aggregator 606 determines the scaled value by analyzing the surface deformation information, the environmental conditions, and/or the operating parameters. For example, the data aggregator 606 generates a weighted value based on different environmental conditions (e.g., air pressure, air temperature, humidity, air density, etc.), operating parameters (e.g., airspeed, altitude, angle of attack, etc.) and/or surface deformation (e.g., density of foreign material, volume, density, area of a foreign material, an area of an opening formed in the aircraft surface, etc.) and/or another parameters. For example, the data aggregator 606 weighs the different parameters and employs an algorithm (e.g., a polynomial equation) to determine a scaled value.

The alert classifier 608 compares (e.g., via the comparator 610) the scaled value to a threshold range (block 814). If the scaled value is less than a lower limit of the threshold range (block 816), the alert classifier 608 initiates an advisory alert (block 818). If the scaled value is greater than an upper limit of the threshold range (block 820), the alert classifier 608 initiates a warning alert (block 822). If the scaled value is within the threshold range, the alert classifier 608 initiates a caution alert (block 824).

Figure 9:
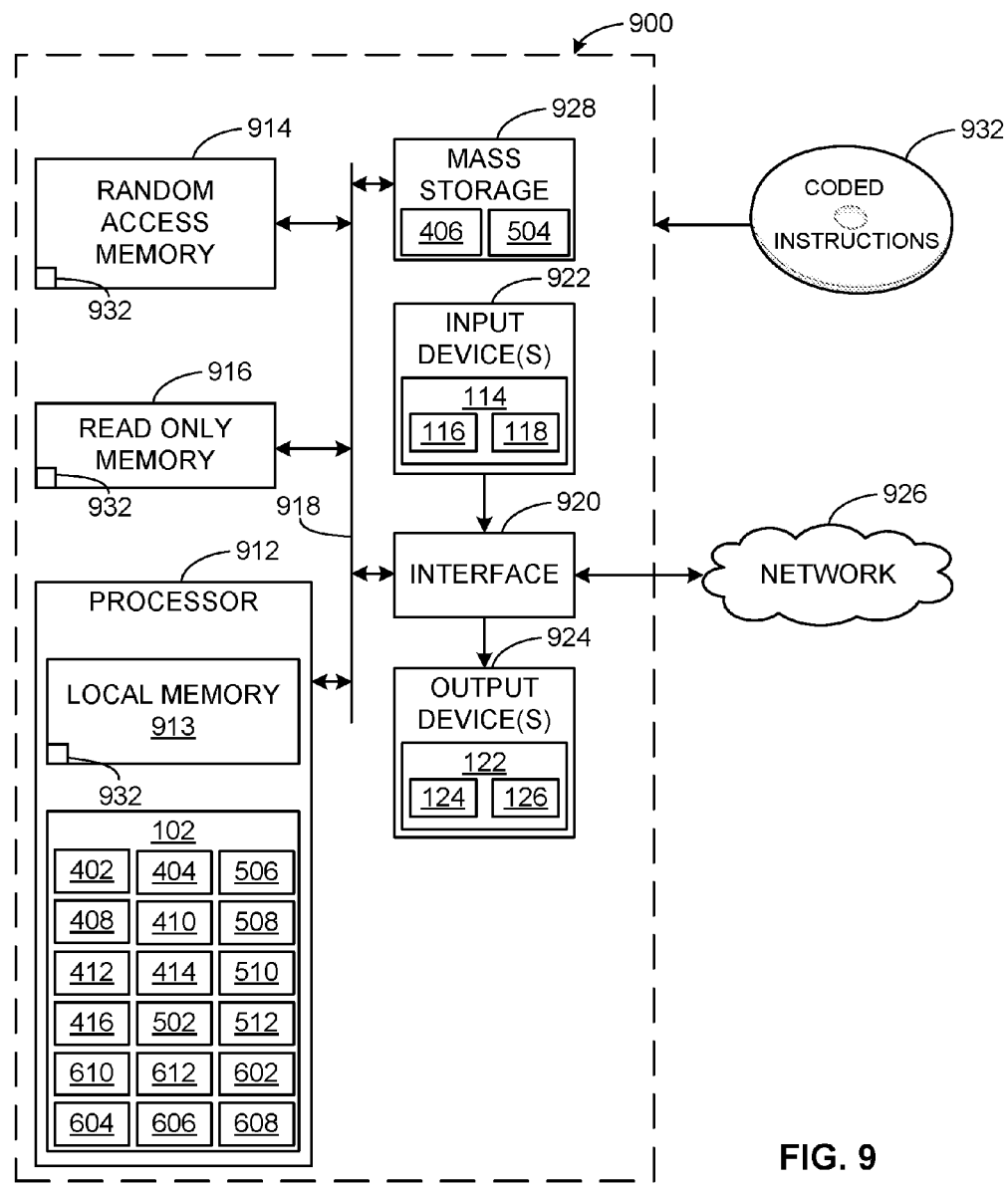
FIG. 9 is a block diagram of an example processor platform 900 capable of executing the methods of FIGS. 7-8 to implement the example surface monitoring system of FIGS. 1-6.

FIG. 9 is a block diagram of an example processor platform 900 capable of executing instructions to implement the methods 700, 800 of FIGS. 7 and 8 and the surface monitoring system 102 of FIG. 1. The processor platform 900 can be, for example, a server, a personal computer, an Internet appliance, or any other type of computing device.

The processor platform 900 of the illustrated example includes a processor 912. The processor 912 of the illustrated example is hardware. For example, the processor 912 can be implemented by one or more integrated circuits, logic circuits, microprocessors or controllers from any desired family or manufacturer.

The processor 912 of the illustrated example includes a local memory 913 (e.g., a cache). The example processor 912 executes instructions to implement the example the example first sensor data register 402, the example second sensor data register 404, the example first sensor data evaluator 408, the example second sensor data evaluator 410, the example obscurant determiner 412, the example alert detector 414, the alert locator 416, the example model generator 502, the example change detector 506, the example substance analyzer 508, the example aircraft parameter analyzer 510, the environmental condition analyzer 512, the example obscurant analyzer 602, the example signal filter 604, the example data aggregator 606, the example alert classifier 608, the example comparator 610 and the example alert generator 612 and/or, more generally, the example surface monitoring system 102 of FIG. 1.

The processor 912 of the illustrated example is in communication with a main memory including a volatile memory 914 and a non-volatile memory 916 via a bus 918. The volatile memory 914 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 916 may be implemented by flash memory and/or any other desired type of memory device. Access to the main memory 914, 916 is controlled by a memory controller.

The processor platform 900 of the illustrated example also includes an interface circuit 920. The interface circuit 920 may be implemented by any type of interface standard, such as an Ethernet interface, a universal serial bus (USB), and/or a PCI express interface.

In the illustrated example, one or more input devices 922 are connected to the interface circuit 920. The input device(s) 922 permit(s) a user to enter data and commands into the processor 912. The input device(s) can be implemented by, for example, an audio sensor, a microphone, a camera (still or video), a keyboard, a button, a mouse, a touchscreen, a track-pad, a trackball, isopoint and/or a voice recognition system. The input device(s) 922 include, but are not limited to, the sensor system 112, the sensors 114, the first sensors 116, the second sensors 118, and the aircraft sensors 120.

One or more output devices 924 are also connected to the interface circuit 920 of the illustrated example. The output devices 924 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 920 of the illustrated example, thus, typically includes a graphics driver card, a graphics driver chip or a graphics driver processor. The output devices 924 may include the output device 122, the crew indicator 124, crew controls (e.g. engine control lever, thrust grip, pedals, etc.) and the display 126.

The interface circuit 920 of the illustrated example also includes a communication device such as a transmitter, a receiver, a transceiver, a modem and/or network interface card to facilitate exchange of data with external machines (e.g., computing devices of any kind) via a network 926 (e.g., an Ethernet connection, a digital subscriber line (DSL), a telephone line, coaxial cable, a cellular telephone system, etc.).

The processor platform 900 of the illustrated example also includes one or more mass storage devices 928 for storing software and/or data. Examples of such mass storage devices 928 include floppy disk drives, hard drive disks, compact disk drives, Blu-ray disk drives, RAID systems, and digital versatile disk (DVD) drives. The mass storage devices 928 may include the example reference model database 406 and the example current reference model database 504.

Coded instructions 932 of FIGS. 7 and 8 may be stored in the mass storage device 928, in the volatile memory 914, in the non-volatile memory 916, and/or on a removable tangible computer readable storage medium such as a CD or DVD.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
    a sensor system to monitor an aircraft surface, the sensor system including a first sensor and a second sensor;
    a surface monitoring system to receive signals from the first sensor and the second sensor, based on the signals received the surface monitoring system is to:
    detect a surface deformation on the aircraft surface;
    analyze one or more environmental conditions or aircraft parameters; and
    classify a severity of a detected surface deformation based on the one or more environmental conditions or aircraft parameters to determine if the detected surface deformation impacts aircraft performance or safety.

2. The apparatus of claim 1, further including an alert detector, the alert detector is to generate a scaled value based on the detected surface deformation and the one or more environmental conditions or aircraft parameters to classify the severity of the detected surface deformation.

3. The apparatus of claim 2, wherein the alert detector is to cause an alert generator to initiate an advisory alert when the scaled value is less than a lower limit of a threshold range, a cautionary alert when the scaled value is within the threshold range, and a warning alert when the scaled value is greater than an upper limit of the threshold range.

4. The apparatus of claim 2, further including a first sensor data evaluator to compare a first reference model of the aircraft surface to a first current model of the aircraft surface provided by the first sensor to detect the surface deformation on the aircraft surface.

5. The apparatus of claim 4, further including a second sensor data evaluator to compare a second reference model of the aircraft surface to a second current model of the aircraft surface provided by the second sensor to detect the surface deformation on the aircraft surface.

6. The apparatus of claim 5, further including an obscurant determiner to detect obscurant conditions.

7. The apparatus of claim 6, wherein the alert detector is to ignore signals from the second sensor data evaluator when the obscurant conditions are greater than a threshold value, and the alert detector is to receive signals from the first sensor data evaluator and the second sensor data evaluator when the obscurant conditions are less than the threshold value.

8. A method comprising:
monitoring an aircraft surface via a first sensor and a second sensor,
receiving signals from the first sensor and the second sensor;
detecting a surface deformation on the aircraft surface based on the received signals;
analyzing one or more environmental conditions or aircraft parameters; and
classifying a severity of a detected surface deformation based on the one or more environmental conditions or aircraft parameters to determine if the detected surface deformation impacts aircraft performance or safety.

9. The method of claim 8, further including generating a scaled value based on the detected surface deformation and the one or more environmental conditions or aircraft parameters to classify the severity of the detected surface deformation.

10. The method of claim 9, further including initiating an advisory alert when the scaled value is less than a lower limit of a threshold range, initiating a cautionary alert when the scaled value is within the threshold range, and initiating a warning alert when the scaled value is greater than an upper limit of the threshold range.

11. The method of claim 9, further including comparing, via a first sensor data evaluator, a first reference model of the aircraft surface to a first current model of the aircraft surface provided by the first sensor to detect the surface deformation on the aircraft surface.

12. The method of claim 11, further including comparing, via a second sensor data evaluator, a second reference model of the aircraft surface to a second current model of the aircraft surface provided by the second sensor to detect the surface deformation on the aircraft surface.

13. The method of claim 12, further including determining obscurant conditions.

14. The method of claim 13, further including ignoring signals from the second sensor data evaluator when the obscurant conditions are greater than a threshold value, and receiving signals from the first sensor data evaluator and the second sensor data evaluator when the obscurant conditions are less than the threshold value.

15. A non-transitory computer-readable medium comprising instructions that, when executed, cause a machine to:
monitor an aircraft surface via a first sensor and a second sensor;
receive signals from the first sensor and the second sensor;
detect a surface deformation on the aircraft surface based on the received signals;
analyze one or more environmental conditions or aircraft parameters; and
classify a severity of a detected surface deformation based on the one or more environmental conditions or aircraft parameters to determine if the detected surface deformation impacts aircraft performance or safety.

16. The computer-readable medium as defined in claim 15 comprising instructions that, when executed, cause the machine to generate a scaled value based on the detected surface deformation and the one or more environmental conditions or aircraft parameters to classify the severity of the detected surface deformation.

17. The computer-readable medium as defined in claim 16 comprising instructions that, when executed, cause the machine to initiate an advisory alert when the scaled value is less than a lower limit of a threshold range, initiate a cautionary alert when the scaled value is within the threshold range, and initiate a warning alert when the scaled value is greater than an upper limit of the threshold range.

18. The computer-readable medium as defined in claim 16 comprising instructions that, when executed, cause the machine to compare, via a first sensor data evaluator, a first reference model of the aircraft surface to a first current model of the aircraft surface provided by the first sensor to detect the surface deformation on the aircraft surface.

19. The computer-readable medium as defined in claim 18 comprising instructions that, when executed, cause the machine to compare, via a second sensor data evaluator, a second reference model of the aircraft surface to a second current model of the aircraft surface provided by the second sensor to detect the surface deformation on the aircraft surface.

20. The computer-readable medium as defined in claim 19 comprising instructions that, when executed, cause the machine to determine obscurant conditions.

21. The computer-readable medium as defined in claim 20 comprising instructions that, when executed, cause the machine to ignore signals from the second sensor data evaluator when the obscurant conditions are greater than a threshold value, and receive signals from the first sensor data evaluator and the second sensor data evaluator when the obscurant conditions are less than the threshold value.

* * * * *